United States Patent [19]

Boudakian

[11] 4,291,165
[45] Sep. 22, 1981

[54] PROCESS FOR MAKING 2-BROMOPYRIDINE

[75] Inventor: Max M. Boudakian, Pittsford, N.Y.

[73] Assignee: Olin Corporation, New Haven, Conn.

[21] Appl. No.: 179,390

[22] Filed: Aug. 18, 1980

[51] Int. Cl.$^3$ .......................................... C07D 213/61
[52] U.S. Cl. .................................................... 546/345
[58] Field of Search ........................................ 546/345

[56] References Cited

U.S. PATENT DOCUMENTS 3,153,045  10/1964  Thomas ............................. 546/345

FOREIGN PATENT DOCUMENTS 54-103873  8/1979  Japan .

OTHER PUBLICATIONS

Craig, *J. Am. Chem. Soc.*, vol. 56, pp. 231–232 (1934).
Organic Synthesis, Coll. vol. III, pp. 136–138 (1955) Editor E. C. Horning, published J. F. Wiley, New York.
Milhailov, *J. Appl. Chem.*, USSR, vol. 27, pp. 331–334 (1954).
Milhailov, *Chemical Abstracts*, vol. 49, entry 3961 (1955).
Chichibabin et al., *Chemical Abstracts*, vol. 10, pp. 2898–2899 (1916).
Boyer et al., *J. Am. Chem. Soc.*, vol. 75, pp. 5298–5300 (1953).
Whitmore et al., *J. Am. Chem. Soc.*, vol. 67, p. 394 (1945).
Giam, "Pyridine and Its Derivatives", Supplement Part III, R. A. Abromovitch, Ed., Interscience, Wiley, N.Y., p. 74 (1974).
Mertel., "Halopyridines", in Pyridine and Its Derivatives., E. Klingsberg, Ed., Part II, Interscience Pub. N.Y. (1961) pp. 379–383.

*Primary Examiner*—John M. Ford
*Attorney, Agent, or Firm*—William A. Simons; Thomas P. O'Day

[57] ABSTRACT

Disclosed is the improvement to the Craig process for producing 2-bromopyridine by the diazotization-bromination reaction of 2-aminopyridine with HBr in the presence of $Br_2$ and a diazotization agent wherein the improvement is to conduct the reaction in the additional presence of $H_2SO_4$ and to employ a molar ratio of HBr:2-aminopyridine in the range from about 1:1 to about 3.5:1 and to employ a molar ratio of $H_2SO_4$:HBr in the range from about 2:8 to about 8:2.

18 Claims, No Drawings

PROCESS FOR MAKING 2-BROMOPYRIDINE

BACKGROUND OF THE INVENTION

1. Field of the Invention

The present invention relates to an improved process for producing 2-bromopyridine.

2. Description of the Prior Art

2-Bromopyridine is a chemical intermediate for many pharmaceutical and pesticidal products.

This compound has been produced by a variety of processes. These processes include the following:

(a) the Craig diazotization-bromination method wherein 2-aminopyridine is first reacted with HBr and $Br_2$ to form a solid orange perbromide; then diazotized with sodium nitrite; followed by a reaction with sodium hydroxide to form the desired 2-bromopyridine [see L. Craig *J. Am. Chem. Soc.*, 56, 232 (1934) and *Organic Synthesis*, Coll. Vol. III, J. F. Wiley, N.Y., p. 136 (1955)];

(b) a modification of the Craig technique wherein 2-aminopyridine is first reacted with HBr and then with $Br_2$ to yield a perbromide solution, then sodium nitrite and HCl are added to the reaction mixture; after which NaOH is added [see G. I. Mikhailov, *Zhur. Priklad. Khim.*, 27, pages 349-351 (1954) and *Chemical Abstracts*, 49, 3961, (1955)];

(c) from 2-aminopyridine by diazotization in a dilute solution of HBr and $HNO_2$ in small yield, the principal product being the corresponding pyridone [see A. E. Chichibabin et al, *J. Russ. Phys. Chem. Soc.*, 46, 1571-89 (1915) and *Chemical Abstracts*, 10, 2898 (1916)];

(d) by reacting vapors of bromine and chlorine with pyridine in the presence of carbon tetrachloride at elevated temperatures to form 2-bromopyridine and 2-chloropyridine simultaneously (see U.S. Pat. No. 3,153,045 which issued to Thomas on Oct. 13, 1964);

(e) by the direct bromination of pyridine [see Wibaut and Den Hertog, *Rec. trav. chim.*, 51, 385 (1932); McElvain and Goese, *J. Am. Chem. Soc.*, 65, 2230 (1943); Wibaut, *Experientia*, 5, 337 (1949)].

(f) from N-methyl-2-pyridone with phosphorus pentabromide and phosphorus oxybromide [See Fischer, *Ber.*, 32, 1303 (1899)].

(g) from sodium 2-pyridinediazotate in solution in concentrated hydrobromic acid [see Chichibabin and Tjashelowa, *J. Russ. Phys. Chem. Soc.*, 50, 495 (1918) (*Chem. Zentr.*, 1923, III, 1021)];

(h) from 2-aminopyridine by diazotization with nitrogen trioxide in 40% hydrobromic acid [see Newman and Fones, *J. Am. Chem. Soc.*, 69, 1221 (1947)];

(i) from 2-chloropyridine by reaction with HBr in the presence of a dehydrated organic solvent (see Japanese Patent Public Disclosure No. 103873).

The preferred method for making 2-bromopyridine has been from 2-aminopyridine by the Craig diazotization-bromination technique or a variation thereof. However, there are certain disadvantages associated with the standard Craig technique. First, the cost of HBr is relatively expensive. Furthermore, it is usually necessary to employ a large molar ratio of HBr to 2-aminopyridine (i.e., more than about 4:1). Thus, the HBr reactant contributes a large proportion of the raw material costs for carrying out this reaction. Besides, 2,5-dibromopyridine may be a significant by-product with the Craig technique.

Also, HBr is generally available in 48% by weight aqueous solutions. Thus, batch productivity is decreased substantially because excessive amounts of 48% HBr are required and large volume equipment also is needed.

As a means of decreasing HBr costs, Mikhailov (see above-noted reference) proposed to substitute concentrated HCl in place of about half of the HBr normally used in the Craig technique. Based on relatively crude boiling point analysis, Mikhailov claimed that no 2-chloropyridine was formed as a by-product. However, as can be seen from the experimental Comparisons 5 and 6 below, the presence of 2-chloropyridine in the 2-bromopyridine product made according to his method was established by using more sophisticated analytical methods (i.e., VPC-mass spectral data). 2-Chloropyridine may be an unacceptable contaminant in 2-bromopyridine for certain pharmaceutical and pesticidal applications.

Accordingly, it is an object of the present invention to improve the Craig technique for making 2-bromopyridine by lowering the amount of HBr needed for that diazotization-bromination reaction; yet not use HCl as a substitute. It is a further objective of the present invention to lower costs and increase productivity of this reaction.

BRIEF SUMMARY OF THE INVENTION

The present invention, therefore, comprises an improvement to the process for producing 2-bromopyridine by the diazotization-bromination reaction of 2-aminopyridine with HBr in the presence of $Br_2$ and a diazotization agent. That improvement is to conduct the reaction in the additional presence of $H_2SO_4$ and to employ a molar ratio of HBr:2-aminopyridine in the range from about 1:1 to about 3.5:1 and to employ a molar ratio of $H_2SO_4$:HBr in the range from about 2:8 to about 8:2.

More specifically, the present invention is directed toward replacing a portion of the relatively expensive HBr with $H_2SO_4$. Thus, this reaction may be carried out more efficiently. Furthermore, this invention does not introduce any undesirable impurities (e.g., chloride ions) into the reaction mixture which might become contaminants for pharmaceutical and pesticidal end-products of 2-bromopyridine.

DETAILED DESCRIPTION

The present invention is an improvement in the conventional Craig technique for producing 2-bromopyridine from 2-aminopyridine. This conventional technique is described in Craig, *J. Am. Chem. Soc.*, 56, pages 231-232 (1934) and *Organic Synthesis*, Coll. Vol. III, J. F. Wiley, N.Y., pages 136-138 (1955). Both of these articles are incorporated herein by reference in their entirety. The Craig technique may be represented by the following reaction:

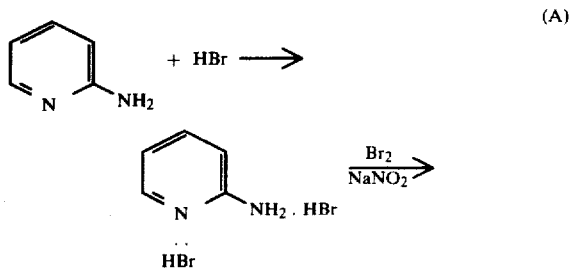

a "Perbromide" $\xrightarrow{\text{NaOH}}$ 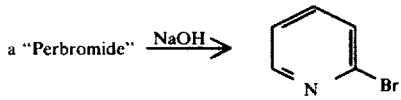

where 2-aminopyridine is first reacted with HBr; then reacted with a diazotization agent, represented here as sodium nitrite, in the presence of bromine to produce a solid orange perbromide compound (whose structure is uncertain). Next, the 2-bromopyridine is formed by addition of a neutralization agent, such as sodium hydroxide, to the reaction mixture.

2-Aminopyridine is a commercially available substance and is prepared by reacting pyridine with sodium amide in ammonia. For the present process, 2-aminopyridine may be used in either solid form or in solution, such as in an aqueous solution.

HBr is also a widely available substance. It is commonly available in 48% by weight aqueous solutions.

An important aspect of the Craig technique is the carrying out of the diazotization reaction in the presence of bromine. The free bromine is necessary to achieve reasonable yields of 2-bromopyridine and hinder the formation of the undesired by-product, 2-hydroxypyridine (also called 2-pyridone). In fact, this latter compound would be the major product if bromine was not added during the reaction. Normally, at least about two moles of $Br_2$ should be employed in the reaction mixture per mole of 2-aminopyridine substrate. Preferably, about 2.0 moles to about 4.0 moles of $Br_2$ is used per one mole of 2-aminopyridine.

Any suitable diazotization agent, preferably, sodium nitrite, may be employed in the reaction. Other diazotization agents for this reaction might include potassium nitrite, nitrous anhydride, nitrous acid, alkyl nitrites such as amyl nitrite, and nitrosyl halide or nitrosyl halide complexes with HBr. Preferably, from about 1 to about 5 moles of a diazotization agent are used per mole of 2-aminopyridine substrate. More preferably, about 1.5 to about 3.5 moles of a diazotization agent are used.

After the diazotization reaction has occured, it is necessary to free the 2-bromopyridine from the "perbromide". This is accomplished simply by adding a sufficient amount of a neutralization agent, such as sodium hydroxide, ammonium hydroxide or the like. The amount of neutralization agent added should be sufficient to raise the pH of the acidic reaction mixture (i.e., to about 7-9) and release or precipitate the 2-bromopyridine in the reaction mixture. Preferably, at least about 5 moles of a neutralization agent should be added per mole of 2-aminopyridine substrate. More preferably, the amount of neutralization agent should be in the range from about 6 to about 15 moles per one mole of the substrate.

As stated above, the present invention is directed at conducting this diazotization-bromination reaction in the additional presence of sulfuric acid. It is surprising that the additional presence of $H_2SO_4$ in the reaction mixture would aid in the formation of 2-bromopyridine. Note Boyer et al. *J. Am. Chem. Soc.*, 75, p. 5298 (1953) teaches that diazotization of 2-aminopyridines in sulfuric acid is a route to 2-hydroxypyridines. The sulfuric acid is used to replace a portion of the more expensive HBr used in this reaction. $H_2SO_4$ acts as a hydrogen ion source during the diazotization reaction. Any concentration of $H_2SO_4$ may be used for the present invention. It is preferred that very concentrated (i.e., above about 90%) aqueous solutions of $H_2SO_4$ be used.

Besides making this reaction more efficient by replacing a portion of the expensive HBr with cheaper $H_2SO_4$, and also, not introducing any undesirable impurities (e.g., chloride ions) into the reaction mixture, this invention has other advantages. For instance, the productivity of the present reaction may be improved because very concentrated $H_2SO_4$ solutions may be employed instead of commonly available 48% by weight solutions of HBr. Also, one mole of $H_2SO_4$ is equivalent to two moles of HBr (i.e., as a hydrogen ion source). Thus, smaller volume reaction vessels may be made employed and more product may be made from comparable amounts of starting materials.

The molar ratio of HBr to 2-aminopyridine substrate for this reaction may be in the range from about 1:1 to about 3.5:1. More preferably, this ratio may be from about 1.1:1 to about 2.5:1. However, it should be noted that the amount of HBr needed from this invention is considerably less than has been disclosed in the prior art methods which used the Craig procedure.

The molar ratio of $H_2SO_4$ to HBr for the present invention may be in the range from about 2:8 to about 8:2. More preferably, from about 2.5:7.5 to about 6:4. Most preferably, from about 3:7 to about 1:1. The use of too little $H_2SO_4$ will not achieve any increase in the efficiency of the reaction; while the replacement of too much HBr with $H_2SO_4$ will effect the yield of 2-bromopyridine product adversely.

The diazotization-bromination reaction of the present invention may be conducted in any suitable manner; for example, it may be desirable to add the bromine and $H_2SO_4$ with the hydrobromic acid to the 2-aminopyridine before the diazotization agent is added, or add the hydrobromic acid, $H_2SO_4$, bromine and diazotization agent sequentially. Still further, it may be desirable to add 2-aminopyridine and the other four substances simultaneously. Preferably, it is advantageous to add the HBr to an aqueous solution (e.g., 50–95% by weight concentration) of 2-aminopyridine at a relatively low temperature (e.g., in the range from about −20° C. to about 10° C., more preferably from about −10° C. to about 0° C.). Next, bromine and $H_2SO_4$ are successively added in the same low temperature range. Then, a diazotization agent such as sodium nitrite is added slowly (e.g., from about 1 to 6 hours) either in an aqueous solution or in pure form at these low temperatures. The reaction should be given sufficient time (e.g., from about 15 minutes to about 300 minutes) to go to completion. After the reaction appears complete or at any desirable time, the 2-bromopyridine is released and recovered from the reaction by the addition of a neutralization agent. This is also preferably carried out in this low temperature range.

It is preferable to operate at atmospheric pressure but lower or higher pressures may be used as desired, for example, 0.5 to 50 atmospheres, advantageously 0.8 to 1.5 atmospheres.

Depending upon the specific method by which the reactants are added to the reaction mixture; the time for completion of the reaction will vary with the speed at which the diazotization agent is added and/or the temperature. The reaction time will increase when the addition is speeded up or with an increase in temperature.

The present process can be carried out in any conventional chemical reactor which is suitable for this purpose. The reactor may be made out of stainless steel glass or plastics such as chlorotrifluoroethylene or tetrafluoroethylene polymers.

The improved Craig diazotization-bromination reaction of the present invention, while eliminating the production of the undesirable by-product, 2-chloropyridine, may still produce relative small amounts of two other by-products which may contaminate final pharmaceutical and pesticidal products. These two by-products are 2,5-dibromopyridine and α-pyridone (2-hydroxypyridine).

2-5-Dibromopyridine is especially difficult to remove from 2-bromopyridine. In the past, those skilled in this art were forced to employ fractional distillation techniques (i.e., slow distillation of the mixture and separate collection of the distillates at each boiling point or after temperature intervals) to remove the 2,5-dibromopyridine. However, the installation of a fractionation column for this purpose is costly.

Accordingly, a preferred embodiment of the present invention contemplates a purification method which avoids the need for fractional distillation; yet, prepares a very pure 2-bromopyridine product which is essentially devoid of 2,5-dibromopyridine (i.e., less than about 0.5% by weight of the total product; more preferably less than 0.2% by weight; most preferably, less than 0.1% by weight).

This preferred purification technique is grounded on the greater basicity of 2-bromopyridine over 2,5-dibromopyridine and features the following sequence of steps:

(a) steam distilling the crude 2-bromopyridine product (which may contain undesirable amounts of impurities like 2,5-dibromopyridine) to form a first organic phase containing the crude 2-bromopyridine product and a first aqueous phase;

(b) phase separating said first organic phase from said aqueous phase;

(c) dissolving the first organic phase in an inert organic solvent;

(d) extracting the dissolved first organic phase with an acidic aqueous solution containing a mineral acid to form a second organic phase and a second aqueous phase containing a 2-bromopyridine salt;

(e) phase separating the second aqueous phase from the second organic phase;

(f) neutralizing the second aqueous phase to release 2-bromopyridine;

(g) steam distilling the neutralized second aqueous phase to form a third aqueous phase and a third organic phase comprising a purified 2-bromopyridine product;

(h) phase separating and recovering the purified 2-bromopyridine product from the third aqueous phase.

In carrying out step (a) of this purification process, any standard technique for steam distilling crude chemical products may be used. The rate and length of time which the steam flows through the crude product are not critical parameters. The type of steam distillation apparatus is likewise not critical.

Step (b) may be carried out by any standard phase separation technique. Decanting is one suitable method.

In step (c), any inert organic solvent which the crude 2-bromopyridine dissolves in without reacting may be used. Also, this solvent should be non-reactive and immiscible with the mineral acid employed in step (d). Suitable inert solvents include methylene chloride, carbon tetrachloride, hexane, heptane, octane and the like. The amount of solvent should be sufficient to completely dissolve the entire crude 2-bromopyridine product.

Instead of carrying out steps (a) and (b), it may be desirable to directly dissolve the crude 2-bromopyridine product into the inert organic solvent. Also, the dissolved crude 2-bromopyridine product may be water-washed before extracted with a mineral acid.

In step (d), the dissolved 2-bromopyridine product is extracted with an aqueous soluton containing a mineral acid. Suitable mineral acids include HCl, HBr, $H_2SO_4$ and $HNO_3$. The preferred mineral acids are HCl and $H_2SO_4$. The concentration of the mineral acid in the aqueous solution may vary. An acceptable concentration of HCl in the aqueous solution may range from about 10% by weight to about 36% by weight. An acceptable concentration of $H_2SO_4$ in the aqueous solution may be from about 10% to about 50% by weight of the solution. It is preferred that at least a 5:1, more preferably, at least a 6:1, molar ratio of mineral acid to the crude 2-bromopyridine product be used to achieve a 90% by weight yield of the purified 2-bromopyridine product. It should be noted that HCl will not react in this step with the 2-bromopyridine to form the undesirable 2-chloropyridine.

Step (e) may be carried out by any standard technique for separating aqueous and organic phases.

Step (f) may be carried out by simply adding a sufficient amount of a neutralization agent to release 2-bromopyridine from the acidified second aqueous phase. Suitable neutralization agents include sodium hydroxide and ammonium hydroxide. The amount of neutralization agent added will depend upon the amount of acid added in the previous step.

Step (g) is a standard steam-distillation step and the resulting third organic phase should consist of essentially 2-bromopyridine [i.e., substantially free (less than 0.5% by weight) of 2,5-dibromopyridine]. It may include a vacuum-topping step whereby a vacuum is attached to the product to remove any traces of water and inert solvent.

By step (h), the purified 2-bromopyridine product is recovered and ready for use in end-product applications.

Besides making 2-bromopyridine, the process of the present invention may be suitable to the preparation of various substituted 2-bromopyridines that could be made by the general Craig procedure. Such substituted 2-bromopyridines would include:

2-bromo-3-picoline
6-bromo-3-picoline
2-bromo-4-picoline
2-bromo-4-ethylpyridine
2-bromo-4-phenylpyridine
2-bromo-2-phenylpyridine
2,5-dibromopyridine The following examples further illustrate the invention. All percentages are by weight unless expressly stated to the contrary.

EXAMPLE 1

2-Aminopyridine (1.0 mole; 80% aqueous solution; 117.6 g.) was added to hydrobromic acid (2.2 moles; 48% aqueous solution; 370 g.) at $-10°$ C. Bromine (2.1 moles; 336 g.) and sulfuric acid (1.0 mole; 93% electrolytic grade; 105.4 g) were successively added at $0°$ C.±5°. Sodium nitrite (2.2 moles; 152 g.) dissolved in 255 ml. water was added over a 2.5 hour period at $0°$ C.±5°. After maintaining the mixture at $0°$ C. for 0.5 hour, 2-bromopyridine was released by addition of sodium hydroxide (9.45 moles; 50% aqueous solution; 756 g.) at 0° C.

Crude 2-bromopyridine (150.8 g.; 93.9% assay; 1.0% H₂O, corresponding to 88.7% analytical yield) was then steam distilled.

Purification was further effected by dissolving crude 2-bromopyridine in methylene chloride (263 g.), followed by addition of hydrochloric acid (5.32 moles; about 15% concentration; 1494 g.) at 0° C. The mixture was stirred at 15°-20° C. for 1.25 hours and the upper aqueous layer phased and neutralized with sodium hydroxide (6.67 moles; 50% aqueous solution; 534 g.). Steam distillation, followed by vacuum-topping at 70° C./20 mm, gave 126 g. of 2-bromopyridine which assayed 99.8% (VPC: 10'×¼" Al Carbowax 20 M column), corresponding to 80% in-hand yield.

This Example presents a preferred method for making 2-bromopyridine according to the present invention and a preferred method for purifying the crude product.

EXAMPLE 2

2-Aminopyridine (1.0 mole; 80% aqueous solution; 117.6 g.) was added to hydrobromic acid (2.2 moles; 48% aqueous solution; 370 g.) at −10° C. Bromine (2.1 moles; 336 g.) was then added at −10° C., followed by sulfuric acid (1.0 mole; 93% electrolytic grade; 105.4 g.). Sodium nitrite (2.2 moles; 152 g.) dissolved in 255 ml. water was added over a 3.75 hour period at 0° C.±5° and held at 0° C. for 50 minutes. 2-Bromopyridine was released by addition of sodium hydroxide (9.45 moles; 50% aqueous solution; 756 g.) at 0° C.

Crude 2-bromopyridine from the neutralized mixture was extracted twice with methylene chlorine (1×241 g.; 1×128 g.) and the organic extract was washed with 500 ml. H₂O. Concentration of an aliquot (216.5 g.) of the methylene chloride extract of the crude 2-bromopyridine product under reduced pressure (70° C./35 mm) gave 74.0 g. of product (95.6% assay of 2-bromopyridine, corresponding to 81.5% analytical yield when corrected for the aliquot used).

However, when another aliquot (192.3 g.) of the methylene chloride extract was extracted with hydrochloric acid (1.2 mole; about 15% solution; 642 g.) and further purified in the manner described in the previous example, a 2-bromopyridine product of 99.1% assay was obtained.

This Example presents an alternative method for purifying the crude 2-bromopyridine product to the purification method of Example 1. This Example, in conjunction with Example 1, also shows the reproductability of the present invention in making a crude 2-bromopyridine product.

EXAMPLE 3

2-Aminopyridine (1.0 mole; 80% aqueous solution; 117.6 g.) was added to hydrobromic acid (1.1 moles; 48% aqueous solution; 185.0 g.) at −10° C. Bromine (2.1 moles; 336 g.) and sulfuric acid (1.5 moles; 93% electrolytic grade; 158.1 g.) were successively added at 0° C.±5°. Sodium nitrite (2.2 moles; 152 g.) dissolved in 255 ml. water was added over a 3 hour period at 0° C.±5°. After maintaining the mixture at 0° C. for 0.5 hour, 2-bromopyridine was released by addition of sodium hydroxide (8.8 moles; 50% aqueous solution; 704 g.) at 0° C.

Steam distillation of the alkaline reaction mixture gave 128.0 g. of crude 2-bromopyridine (83.0% assay, 1.01% H₂O, corresponding to 66.6% analytical yield).

This Example, compared to the two previous Examples, substituted more HBr by H₂SO₄ in carrying out the reaction. The results show a reduction in 2-bromopyridine yield occurs when too much HBr was replaced by H₂SO₄.

COMPARISON 1

2-Aminopyridine (1.0 mole; 94 g.) was added to hydrobromic acid (4.4 moles; 48% aqueous solution; 740 g.) at −10° C. Bromine (2.1 moles; 336 g.) was added to the above solution of 2-aminopyridine hydrobromide at −5° C. to give a yellow-orange "perbromide" paste. Sodium nitrite (2.2 moles; 152 g.) dissolved in 255 ml. water was added over a 1.5 hour period at −5° to −10° C.; nitrogen and some brown fumes were evolved. The mixture was maintained at 0° C. for 1.5 hours and 2-bromopyridine was released by addition of sodium hydroxide (756 g.; 50% aqueous solution; 9.45 moles) at 0° C. The reaction mixture was steam distilled and the organic phase of the steam-distilled product was vacuum-topped (95° C./40 mm), wt. 149.7 g. VPC assay (10% Carbowax 20 M column/180° C.): 96.1% 2-bromopyridine, corresponding to 90.6% yield.

This product is contaminated with 2.3% of high boilers which were identified by trapping and identified via gas chromatography/mass spectroscopy (15% Carbowax 20 M on CW NAW programmed from 80°-220° C. at 8°/min.): Dibromopyridine Isomer I (2,5)>>>Dibromopyridine Isomer II>Tribromopyridine(s).

This Comparison describes the conventional Craig procedure for preparing 2-bromopyridine by the diazotization/bromination of 2-aminopyridine. As can be seen, 4.4 moles of HBr are used per mole of 2-aminopyridine. This is twice as much HBr as is used in Example 1.

COMPARISON 2

2-Aminopyridine (1.0 mole; 94 g.) was added to hydrobromic acid (4.4 moles; 48% aqueous solution; 740 g.) at −10° C. Bromine (2.1 moles; 336 g.) was added to the above solution at −10° C. Sodium nitrite (2.2 moles; 152 g.) dissolved in 255 ml. water was added over a 2.3 hour period at −5° C. The mixture was held at 5° C. for 0.6 hour and 2-bromopyridine was released by addition of sodium hydroxide (756 g.; 50% aqueous soluton; 9.45 moles) at 0° C. Crude 2-bromopyridine (94.4% assay; 139.4 g.; 88.2% analytical yield) was steam distilled.

Purification was further effected by dissolving the steam distilled crude 2-bromopyridine in methylene chloride (241 g.), followed by addition to hydrochloric acid (5.1 moles; about 15% aqueous solution; 1455 g.) at 0° C. The mixture was then successively stirred (1.5 hours/20° C.) and the two layers separated.

The aqueous layer (1725 g.) was neutralized with 50% aqueous solution of sodium hydroxide and steam distilled to give 123.9 g. (0.784 mole) of product which assayed 99.9% (VPC: 10'×¼" Al Carbowax 20 M column), corresponding to 78.4% in-hand yield of 2-bromopyridine.

This Comparison describes the conventional Craig procedure for preparing 2-bromopyridine along with a preferred method of purifying the crude product. Comparing Example 1 with this Comparison shows that the process of the present invention achieves approximately the same product assays and yields as the Craig procedure; yet, with half the amount of HBr.

COMPARISON 3

2-Aminopyridine (1.0 mole; 94 g.) was added to 48% hydrobromic acid (2.2 moles; 370 g.) at −10° C. Bromine (2.1 moles; 336 g.) was added to the above solution at −10° C. Sodium nitrite (2.2 moles; 152 g.) dissolved in 255 ml. water was added over 2 hour period at −5° C. This mixture was held at 0° C. for 1 hour.

The mixture was neutralized by addition of sodium hydroxide (9.45 moles; 50% aqueous solution; 756 g.) at 0° C. Crude 2-bromopyridine was steam distilled, wt. 145.0 g. The product assayed 84.0% 2-bromopyridine, corresponding to 76.3% analytical yield. The balance of the crude product contained significant amounts of high-boilers (15.3%).

This Comparison, in conjunction with Comparisons 1 and 2, show the assays and yields decrease significantly when the standard Craig procedure is followed, except with less than about 4:1 molar ratio of HBr:2-aminopryidine. Also, the amount of high boiler contamination of the 2-bromopyridine product occurs (from 2–5% to 15%) when less HBr is used. In other words, this Comparison shows that some hydrogen ion source is required to replenish the supply of needed hydrogen ions removed by elimination of 2.2 moles HBr.

COMPARISON 4

2-Aminopyridine (1.0 mole; 80% aqueous solution; 117.6 g.) was added to 48% hydrobromic acid (4.4 moles; 740 g.) at −10° C. The "perbromide" was formed by addition of bromine (2.1 moles; 336 g.) to 2-aminopyridine hydrobromide at −10° C. Diazotization was accomplished by addition of sodium nitrite (2.2 moles; 152 g.) dissolved in 231.5 g. $H_2O$ over a 2.1 hour period at −5° C.; nitrogen was evolved throughout this period. After stirring at 0° to 20° C. (2 hrs.) to complete diazotization, 2-bromopyridine was liberated by addition of 50% sodium hydroxide (756 g.; 9.45 moles) at 0° C.

The crude product was extracted twice from the yellow product mixture by stirring with methylene chloride (20° C.) (1×241 g.; 1×127.5 g.). Separation of the organic (upper) and aqueous layers was rapid. The combined organic extract (785 g.) was washed with water (250 g.) to remove occluded inorganics. The organic product (530.5 g.) was extracted with 13% hydrochloric acid (6.0 moles; 1685 g.) for 0.5 hour at 10° C.

The lower organic layer (283.5 g.) was concentrated to a solid (m.p. 64°–90° C.), wt. 15.0 g.

The aqueous layer (935 g.) was neutralized with 50% sodium hydroxide (537 g.) (pH 12) and 2-bromopyridine steam-distilled. Vacuum-topping (95° C./40 mm) gave 126.7 g. (0.802 mole) of product, which assayed 99.1% 2-bromopyridine (the balance consisted of $CH_2Cl_2$, 0.8%; 2.5-dibromopyridine, 0.1%). The yield of 2-bromopyridine was 80.2%.

This Comparison, in conjunction with Example 2, shows that the process of the present invention, using an alternative purification method, achieves the same 2-bromopyridine product assay while using one-half of the HBr.

COMPARISON 5

2-Aminopyridine (1.0 mole; 94 g.) was added to 48% hydrobromic acid (2.2 moles; 370 g.) at −10° C. Bromine (2.1 moles; 336 g.) was added to the above solution at −5° C. to give a yellow-orange "perbromide" paste.

Hydrochloric acid (1.65 moles; 32% aqueous solution; 188.2 g) was added at −10° C. Sodium nitrite (2.2 moles; 152 g.) dissolved in 255 ml. water was added over a 2.80 hour period at −5° to −10° C.; nitrogen and some brown fumes were evolved. The mixture was maintained at 0° C. for 0.5 hour and 2-bromopyridine was released by addition of 50% aqueous solution sodium hydroxide at 0° C.

The reaction mixture was steam-distilled and the organic phase (wt. 146.5 g.; 1.1% $H_2O$) separated: VPC assay-2-bromopyridine, 94.5% (corresponding to 86.4% yield). The balance of the crude product consisted of 2-chloropyridine (2.6%) and 2,5-dibromopyridine (2.8%). These were identified by gas chromotography/mass spectroscopy.

This Comparison shows that the Mikhailov procedure, without extensive purification, results in a crude 2-bromopyridine product which is contaminated with a relatively large amount of 2-chloropyridine (2.6% by weight).

COMPARISON 6

2-Aminopyridine (1.0 mole; 80% aqueous solution; 117.6 g.) was added to hydrobromic acid (2.2 moles; 48% aqueous solution; 370 g.) at −10° C. The "perbromide" was formed by addition of bromine (2.1 moles; 336 g.) to 2-aminopyridine hydrobromide at −10° C. Hydrochloric acid (32%, 188.2 g. corresponding to 1.65 moles) was added at −4° C. Diazotization was accomplished by addition of sodium nitrite (2.2 moles; 152 g.) dissolved in 255 ml $H_2O$ over a 2.5 hour period at −5° C.; nitrogen was evolved throughout this period. After stirring at 0° C. for 1 hour, 2-bromopyridine was liberated by addition of 50% NaOH (756 g.; 9.45 moles) at 0° C.

The crude product was extracted twice from the yellow product mixture by stirring the methylene chloride (25° C.) (1×241 g.; 1×128 g.). Separation of the organic (upper) and aqueous layer was rapid. The combined organic extract (500 g.) was washed with water (250 ml.). The organic product (428 g.) was extracted with hydrochloric acid (6.0 moles; 13% aqueous solution; 1685 g.) for 1 hour at 25° C.

The lower organic layer (229 g.) was concentrated to a solid, wt. 10.4 g. (m.p. 51°–52° C.).

The aqueous layer was neutralized with 50% sodium hydroxide (536.5 g.; 6.7 moles) (pH>12) and 2-bromopyridine steam-distilled. The organic layer (wt. 130.0 g.) of the steam-distilled product was vacuum-topped (82° C./10 mm) and gave a product with the following assay (VPC):

| | |
|---|---|
| low boiling fraction ($CH_2Cl_2$) | 1.3% |
| medium boiling fraction (2-chloropyridine) | 1.0% |
| main fraction (2-bromopyridine) | 97.4% |
| high boiling fraction (mainly 2,5-dibromopyridine) | 0.3% |
| | 100.0% |

The yields of 2-bromopyridine and 2-chloropyridine in this first vacuum-topped product were 80.1% and 1.1%, respectively.

The main fraction was again vacuum-topped (82° C./10 mm) to give a second product with the following assay (VPC):

| | |
|---|---|
| 2-chloropyridine | 0.6% |
| 2-bromopyridine | 99.0% |
| high boilers, mainly | |
| 2,5-dibromopyridine | 0.4% |
| | 100.0% |

This Comparison shows that the Mikhailov procedure results in a 2-bromopyridine product contaminated with 2-chloropyridine, even when extensive purification procedures have been carried out. The presence of even 0.6% 2-chloropyridine in a 2-bromopyridine product may have an unfavorable effect if the product is to be used for some pharmaceutical use.

What is claimed is:

1. In the process for producing 2-bromopyridine by the diazotization-bromination reaction of 2-aminopyridine with HBr in the presence of $Br_2$ and a diazotization agent, wherein the improvement comprises:
    conducting said reaction in the additional presence of $H_2SO_4$, employing a molar ratio of HBr:2-aminopyridine in the range from about 1:1 to about 3.5:1, and employing a molar ratio of $H_2SO_4$:HBr in the range from about 2:8 to about 8:2.

2. The process of claim 1 wherein at least about 2 moles of $Br_2$ are employed per mole of 2-aminopyridine.

3. The process of claim 1 wherein said diazotization agent is selected from the group consisting of sodium nitrite, potassium nitrite, nitrous anhydride, nitrous acid, alkyl nitrite, nitrosyl halide, and nitrosyl halide complexes with HBr.

4. The process of claim 1 wherein from about 1 to about 5 moles of said diazotization agent are employed per one mole of 2-aminopyridine.

5. The process of claim 1 wherein said diazotization agent is sodium nitrite.

6. The process of claim 1 wherein said $H_2SO_4$ is an aqueous solution having a concentration above 90% by weight $H_2SO_4$.

7. The process of claim 1 wherein said molar ratio of HBr:2-aminopyridine is in the range from about 1.1:1 to about 2.5:1.

8. The process of claim 1 wherein said molar ratio of $H_2SO_4$:HBr is in the range from about 2.5:7.5 to about 6:4.

9. The process of claim 1 wherein diazotization-bromination reaction is carried out at a temperature in the range from about −20° C. to about 10° C.

10. The process of claim 1 wherein a purified 2-bromopyridine product is prepared by a purification process comprising:
    (a) steam-distilling a crude 2-bromopyridine product that is recovered from the diazotization-bromination reaction mixture to form a first organic phase containing said crude 2-bromopyridine product and a first aqueous phase;
    (b) phase separating said first organic phase from said first aqueous phase;
    (c) dissolving the first organic phase in an inert organic solvent;
    (d) extracting the dissolved organic phase with an acidic aqueous solution containing a mineral acid to form a second organic phase and a second aqueous phase containing a 2-bromopyridine salt;
    (e) phase separating said second aqueous phase from said second organic phase;
    (f) neutralizing the second aqueous phase to release 2-bromopyridine;
    (g) steam-distilling the neutralized second aqueous phase to form a third aqueous phase and a third organic phase comprising a purified 2-bromopyridine product;
    (h) phase separating and recovering said purified 2-bromopyridine product from said third aqueous phase.

11. The process of claim 10 wherein said inert organic solvent employed in step (c) is methylene chloride.

12. The process of claim 10 wherein said mineral acid employed in step (d) is HCl having a concentration from about 10% to about 36% by weight.

13. The process of claim 10 wherein the molar ratio of mineral acid to crude 2-bromopyridine product is at least about 5:1.

14. In the process for producing 2-bromopyridine by the diazotization-bromination reaction of 2-aminopyridine with HBr in the presence of $Br_2$ and a diazotization agent, wherein the improvement comprises:
    conducting said reaction in the additional presence of $H_2SO_4$, employing a molar ratio of HBr:2-aminopyridine in the range from about 1.1:1 to about 2.5:1, and employing a molar ratio of $H_2SO_4$:HBr in the range from about 3:7 to about 1:1.

15. The process of claim 14 wherein about 2 to about 4 moles $Br_2$ are employed per 1 mole of 2-aminopyridine.

16. The process of claim 15 wherein about 1.5 to about 3.5 moles of said diazotization agent are employed per 1 mole of 2-aminopyridine.

17. The process of claim 16 wherein said diazotization agent is sodium nitrite.

18. The process of claim 17 wherein said $H_2SO_4$ is employed in a concentration above about 90% by weight.

* * * * *